United States Patent [19]

Boyd et al.

[11] Patent Number: 5,425,773
[45] Date of Patent: Jun. 20, 1995

[54] INTERVERTEBRAL DISK ARTHROPLASTY DEVICE

[75] Inventors: Lawrence M. Boyd, Memphis, Tenn.; Richard M. Salib, Excelsior, Minn.; Kenneth A. Pettine, Fort Collins, Colo.

[73] Assignee: Danek Medical, Inc., Memphis, Tenn.

[21] Appl. No.: 223,119

[22] Filed: Apr. 5, 1994

[51] Int. Cl.$^6$ .................................. A61F 2/44
[52] U.S. Cl. .............................. 623/17; 623/18
[58] Field of Search ...................... 623/16, 17, 18

[56] References Cited

U.S. PATENT DOCUMENTS

| | | |
|---|---|---|
| Re. 32,449 | 6/1987 | Claussen et al. . |
| 4,349,921 | 9/1982 | Kuntz ........................... 3/1 |
| 4,394,921 | 9/1982 | Kuntz . |
| 4,595,663 | 6/1986 | Krohn et al. . |
| 4,714,469 | 12/1987 | Kenna . |
| 4,759,769 | 7/1988 | Hedman et al. . |
| 4,846,840 | 7/1989 | Leclercq et al. ............ 623/23 |
| 4,863,476 | 9/1989 | Shepperd . |
| 4,932,975 | 6/1990 | Main et al. . |
| 4,936,848 | 6/1990 | Bagby . |
| 4,946,378 | 8/1990 | Hirayama et al. . |
| 4,997,432 | 3/1991 | Keller ........................ 606/61 |
| 5,002,576 | 3/1991 | Fuhrmann et al. . |
| 5,037,438 | 8/1991 | Davidson . |
| 5,047,055 | 9/1991 | Bao et al. . |
| 5,071,437 | 12/1991 | Steffee . |
| 5,258,031 | 11/1993 | Salib et al. ................... 623/17 |
| 5,314,478 | 5/1994 | Oka et al. ..................... 623/18 |

FOREIGN PATENT DOCUMENTS

WO92/14423 9/1992 WIPO .
WO93/10725 6/1993 WIPO .

*Primary Examiner*—David Isabella
*Assistant Examiner*—Laura Fossum
*Attorney, Agent, or Firm*—Woodard, Emhardt, Naughton, Moriarty & McNett

[57] ABSTRACT

A disk arthroplasty device (310) is provided for replacement of a spinal disk. The device is implantable into a resected disk space and is formed with ball (346) and socket (326) members and shaped to provide lateral bending and backward extension of up to about 5° and forward flexion of up to about 15°. Four embodiments (10), (110), (210) and (310) permit up to about 5° axial rotation and a fifth embodiment (410) permits unrestricted axial rotation. Metal insert cups (70) and (170) are provided for attaching to the device surfaces and are convexly shaped along one axis to conform to the natural contours of the top and bottom vertebra surfaces. The metal insert cups (70) and (170) provide tensile support to the structure and provide for the attachment of additional structures for retaining the device in position after implantation into a disk space.

16 Claims, 9 Drawing Sheets

INTERVERTEBRAL DISK ARTHROPLASTY DEVICE

BACKGROUND OF THE INVENTION

The present invention is directed to a surgical joint replacement device; particularly, a replacement for a degenerated or ruptured disk between consecutive vertebrae in the spine.

Currently there are approximately 60,000 lumbar spine fusions performed in the United Skates and 30,000 lumbar fusions performed in Canada each year. Spinal fusion is frequently used as a treatment for low back pain and intervertebral disk degeneration, and the use of internal fixation has increased the ability of a surgeon to obtain a solid fusion. There is increased concern, however, that the biomechanical rigidity of the fusion and internal fixation may predispose adjacent spinal motion segments to rapid deterioration. Long-term follow up of patients undergoing a successful fusion indicates that 50 percent will continue to have complaints of pain. As in other joints, alternatives to fusing a spinal motion segment have inherent advantages.

Researchers have attempted to design a successful intervertebral disk arthroplasty device for years. U.S. Pat. No. 4,946,378 discloses an artificial disk having a pair of end bodies with a medical synthetic polymeric intermediate member held between the end bodies. The intermediate member apparently provides some flexibility. Somewhat similarly, U.S. Pat. No. 5,002,576 discloses an artificial disk having end cover plates separated by a closed corrugated tube which is filled with a viscoelastic material, like a body-compatible silicone. Also, U.S. Pat. No. 4,932,975 shows a vertebral prosthesis having a pair of end members that house suspension plates surrounded by an elastomeric medium. The end housings are interconnected with flexible and expandable bellows.

Other approaches are shown in U.S. Pat. Nos. 4,349,921, 4,714,469, 4,759,769, 4,863,476, 4,936,848, 4,997,432, 5,047,055, 5,071,437 and PCT Patent WO 92/14423. U.S. Pat. No. 4,349,921 discloses an artificial disk having convex superior and inferior surfaces corresponding to the adjacent vertebrae surfaces and being formed from two components to allow flexion and extension between the two components. U.S. Pat. No. 4,714,469 discloses a single member artificial disk having a predetermined thickness. U.S. Pat. No. 4,759,769 discloses an artificial disk having upper and lower members hinged together at a rear portion and biased apart at a front portion by stiff coil springs. U.S. Pat. No. 4,863,476 discloses a two portion spinal implant that is expandable so as to increase the spacing between the adjacent vertebrae. U.S. Pat. No. 4,936,848 shows an artificial disk having a spherical shape that is hollow and rigid. The sphere wall contains fenestrations, open to the sphere cavity, for placing bone fragments therein. U.S. Pat. No. 4,997,432 shows an artificial disk having plates separated by a sliding core body normally consisting of a synthetic material. U.S. Pat. No. 5,047,055 discloses an artificial disk made from a hydrogel material having a specified compressive strength and, when hydrated, having the shape of a human disk. U.S. Pat. No. 5,071,437 shows an artificial disk having two rigid end-plates separated by, and connected to, an elastomeric core material having flexure properties similar to those of a human disk.

Finally, U.S. Pat. Nos. 4,595,663, Re. 32,449 and 5,037,438 disclose the use of ceramic material, including zirconia, for applications such a joint replacement.

There are certain basic criteria a successful intervertebral disk arthroplasty device must fulfill. Fatigue strength of the materials is of utmost importance. Since the average age of patients undergoing spinal fusion is 42 years old, the life span of the device should exceed 40 years. Assuming the average person experiences 2 million strides per year and 125,000 significant bends in the spine, a conservative estimate of the number of spinal loading cycles over the 40-year period would be 85 million cycles. To provide a factor of safety, the device should be designed to at least a fatigue limit of 100 million cycles.

In addition to such durability, the materials for a successful intervertebral disk arthroplasty device must be biocompatible. The amount of wear of the implant must be kept to a minimum. Although the implant should be small enough to be contained within the anatomic confines of a normal disk space, it is recognized that it may be advantageous to increase the prosthetic disk height in order to over distract the disk space to unload the facet joints posteriorly.

The present invention not only satisfies these criteria, but it is anticipated that it could be a successful arthroplasty in place of 90 percent of the fusions currently being performed.

SUMMARY OF THE INVENTION

The present invention is directed to an intervertebral disk arthroplasty device comprising a first member having a socket portion and a second member having a ball portion fitting in the socket portion. With respect to a space created by a resected disk from between first and second vertebrae, the first member fits adjacent the first vertebrae and the second member fits adjacent the second vertebrae so that the ball portion fits in the socket portion.

In one embodiment, a first base plate having a first tab is fastened to the first member and a second base plate having a second tab is fastened to the second member. Screws are passed through the first and second tabs to fasten the base plates, and their corresponding first and second members, to the adjacent vertebrae.

In another embodiment, first and second members are fastened to metal insert cups, preferably made of titanium. The use of titanium insert cups offers several advantages, including: (1) providing tensile support to the structure and maintaining the first and second member material in compression, (2) providing for the attachment of resisting fins to the anterior ends of the outer surface of an insert cup to further resist axial rotation by known processes such as machining, soldering, welding or gluing, (3) providing a surface that coatings may easily adhere to, such as a titanium Dead coating for promoting bony ingrowth fixation using known technologies such as sintering or spraying and (4) providing a structure wherein the first and second members can remain a single size while the insert cup sizes may be more easily and cheaply varied by either adding or reducing metal thickness.

The invention also contemplates instances where initial screw fixation may not be necessary. It has been shown that bone ingrowth can occur into ceramic. Thus, in one aspect of the invention, a preferred material for the first and second members is zirconium oxide ceramic or aluminum oxide ceramic. The indicated ceramic is biocompatible and the fatigue strength is expected to provide the necessary number of design cycles for the indicated use. Wear would be minimal and the implant can be made small enough to fit within the anatomic confines of a normal disk space. Although zirconium oxide ceramic or aluminum oxide ceramic are presently preferred, it is understood that other materials may be found which will also satisfy performance needs.

In any case, with material criteria satisfied, the invention then further provides for movement with up to 3 degrees of freedom mimicking normal intervertebral disk movement, except for compression. In one preferred embodiment, the disk arthroplasty device is shaped to provide up to 15 degrees of flexion, 5 degrees of extension 5 degrees of lateral bending, while restricting anterior/posterior shear, axial rotation and axial compression movements. In another embodiment, the device is shaped to provide the 3 degrees of movement described above and to provide unlimited axial rotation. The inventive arthroplasty device is designed to be non-compressible in order to maintain distraction of the facet joints posteriorly, thereby reducing the likelihood of a source of possible pain.

The arthroplasty device is placed in a distracted disk space so that the surrounding soft-tissue, ie. disc annulus, is in tension, to prevent the arthroplasty device from dislocating. In this environment, the ball and socket portions as defined by the invention eliminate any loose moving parts, while still providing for the greatest flexibility of movement available.

Thus, the advantages and objects obtained by the present invention are many. Further explanation and understanding is available by reference to the drawings briefly described hereinafter and to the detailed description thereafter.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
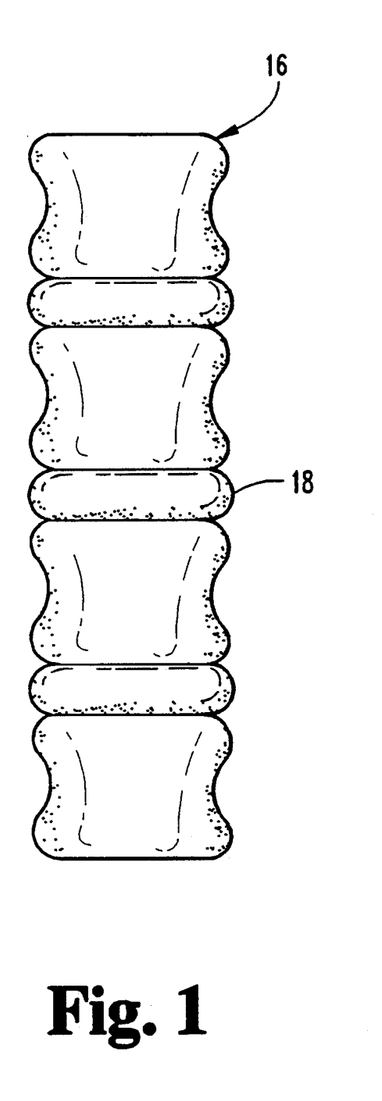
FIG. 1 is a front representation of a lumbar spine showing healthy disks between vertebral bodies.
Figure 2:
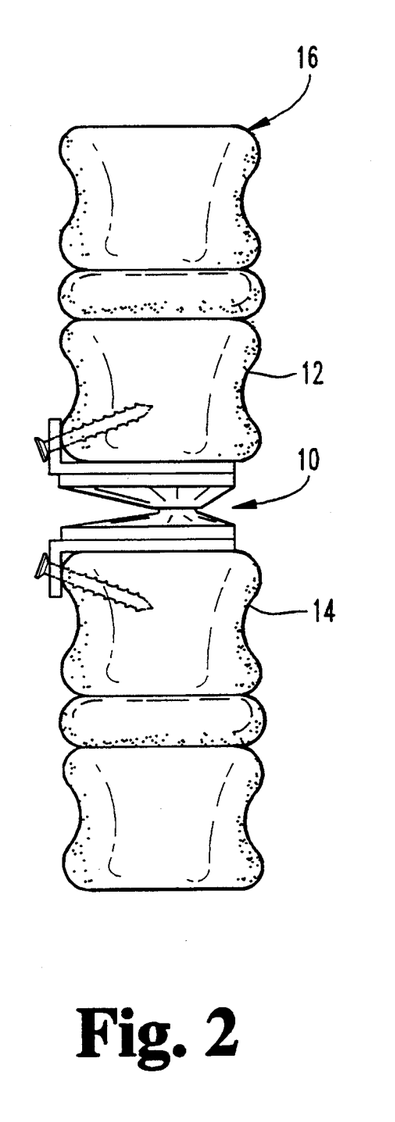
FIG. 2 is similar to FIG. 1, except a disk has been replaced by a disk arthroplasty device in accordance with the present invention.

Referring now to FIGS. 1–4 wherein like reference numerals designate identical or corresponding parts throughout the several views, and more particularly to FIG. 2, an intervertebral disk arthroplasty device in accordance with the present invention is designated generally by the numeral 10. Device 10 is shown implanted between a first vertebral body 12 above it and a second vertebral body 14 below it, all being part of a representative lumbar spinal column 16. Lumbar spine 16 is shown in FIG. 1 to include a healthy disk 18. Device 10 is a prosthetic disk replacement in the space created by resected disk 18.

Figure 3:
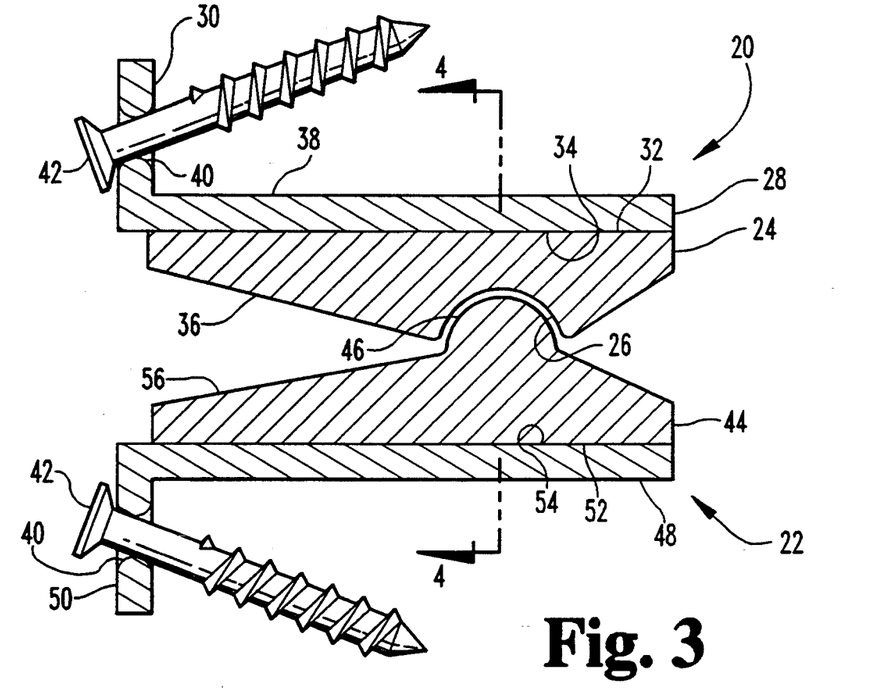
FIG. 3 is a side cross-sectional view of a disk arthroplasty device in accordance with one embodiment of the present invention.
Figure 4:
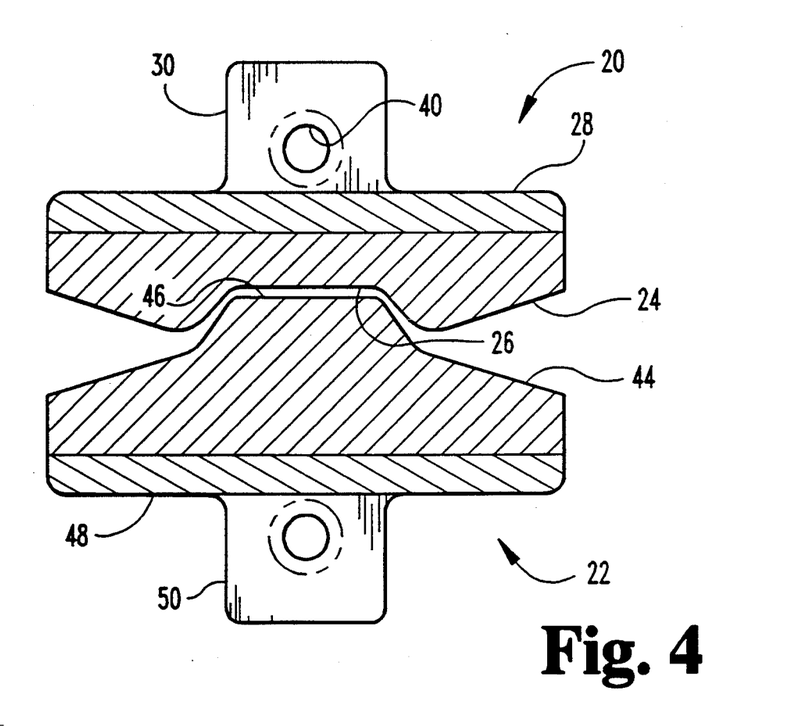
FIG. 4 is a front view of the device of FIG. 3.

As shown in FIGS. 3 and 4, disk arthroplasty device 10 includes an upper assembly 20 and a lower assembly 22. Upper assembly 20 includes a first member 24 having a socket 26 therein. A base plate 28 having an upwardly extending tab 30 therefrom is fastened to first member 24. First member 24 has an upper side 32 to conform with and be fastened to an adjacent side 34 of base plate 28. A side 36 opposite upper side 32 includes socket 26 formed therein. Side 36 is formed so that it slopes upwardly on all sides of socket 26 such that the sloping is away from the entrance to socket 26 and toward upper side 32.

Base plate 28 is essentially a flat plate fastened with a biocompatible adhesive or other fastening mechanism known to those skilled in the art along side 34 to side 32 of first member 24. The upper side 38 of base plate 28 is formed to conform with vertebral body 12. Generally, side 38 is flat, and the conforming side 40 of vertebral body 12 is made flat during the surgery. Tab 30 extends upwardly and is integral with base plate 28. Tab 30 includes an opening 40 therethrough so that a screw 42 (shown with respect to lower base plate 48) can be used to fasten assembly 20 to vertebral body 12.

Lower assembly 22 includes a second member 44 having a ball 46 formed thereon which fits loosely into socket 26. Base plate 48 having tab 50 is similar to upper base plate 28 with tab 30 and need not be described further. First member 44 has a lower side 52 which is fastened to an adjacent side 54 of base plate 48 and in a similar fashion as earlier described with respect to first member 24 and upper base plate 28. A side 56 opposite from lower side 52 includes ball 46 extending upwardly therefrom. Side 56 slopes away from ball 46 on all sides of ball 46 so as to create space between first and second members 24, 44 except where they fit together at ball 46 and socket 26. In one preferred embodiment, sides 56 and 36 slope away from ball 46 and socket 26 along an inclined plane in four different directions. Ball 46 and socket 26 generally have an oval shape or an elongated shape with quarter spherical shapes at the ends.

A motion segment with respect to the present invention comprises a disk arthroplasty device 10 and adjacent upper and lower vertebral bodies. The exact contours of ball 46 and socket 26 and and the surrounding surfaces of sides 36 and 56 determine the range of motion allowed in flexion and extension, side bending, shear and rotation of the motion segment.

The primary motion observed in a healthy lumbar intervertebral joint is flexion-extension. A typical L4-L5 intervertebral disk allows 13 degrees of flexion, 3 degrees of extension, 3 degrees of lateral side bending, 1 degree of axial rotation, and a small amount of shear. The center of rotation for flexion-extension is located in the posterior portion of the intervertebral disk space. The present invention is based on a concept of loose constraint. One preferred embodiment allows 3 degrees of freedom mimicking the normal intervertebral disk movements of flexion, extension and lateral bending. Axial rotation, anterior/posterior shear and axial compression are restricted by disk arthroplasty device 10 in order to protect the posterior facet joints. In addition, it is inserted by distracting the disk space which will place the surrounding soft tissue constraints in tension. This helps prevent the arthroplasty device from dislocating. The device is shaped to provide 15 degrees of flexion, 5 degrees of extension, 5 degrees of side bending, 5 degrees of rotation, and 2 millimeters of shear. The articulating surfaces are the concave female socket surface which articulates with the male concave ball surface. Such design eliminates loose moving parts.

The present invention contemplates the use of a material for the first and second members 24 and 44 that will result in low particulate generation and that will prevent axial movement in compression. This application appears to be well suited for ceramic materials and one preferred embodiment uses zirconium oxide as the ceramic material while another preferred embodiment uses aluminum oxide. The material specifications show ideal wear characteristics and biocompatibility. The modulus of elasticity is less than previously available ceramics, and is less prone to cracking. It would appear that the material would last the required 40 years as a replacement disk arthroplasty.

The present invention as disclosed in FIGS. 1-4 has the ceramic members 24 and 44 fastened to base plates made preferably from either chrome cobalt or titanium. The purpose for the metal base plates is to enhance bone ingrowth for long-term fixation and to provide for short term fixation with screw attachments to adjacent vertebral bodies. However, it is understood that since device 10 is placed in distracted disk space wherein surrounding soft tissue constraints are in tension, that initial screw fixation may not be necessary. Furthermore, bone ingrowth has been shown to occur into ceramic. It is anticipated, therefore, that the entire disk arthroplasty device may be able to be made of only first and second members, 24 and 44, namely the two articulating pieces of ceramic.

An appropriate surgical technique for implacement of the present invention is described in a paper, incorporated herein by reference, entitled "Femoral Cortical Ring Plus Cancellous Dowel: An Alternative in an Anterior Lumbar Interbody Fusion" available from Richard M. Salib, M.D., Institute for Low Back Care, 2800 Chicago Avenue South, Minneapolis, Minn. 55407.

Figures 5, 6, 7:
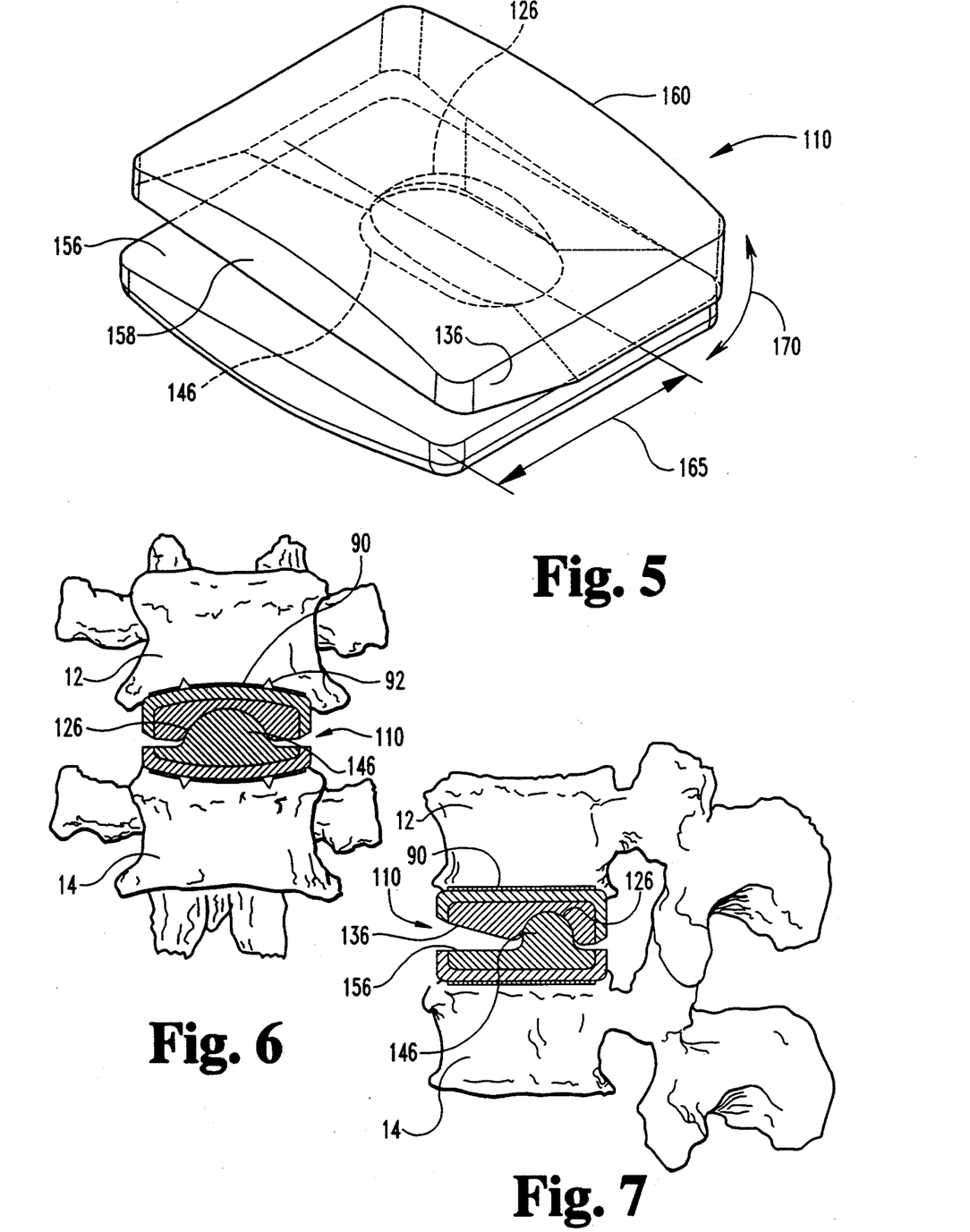
FIG. 5 is a perspective view of a disk arthroplasty device in accordance with a further embodiment of the invention with the ball and socket configuration shown in phantom.
FIG. 6 is an anterior view of two vertebrae showing replacement of a human disk by a disk arthroplasty device in accordance with another embodiment of the present invention.
FIG. 7 is a side view of FIG. 5.

FIGS. 5-14 show additional embodiments of a disk arthroplasty device according to the present invention. Referring to FIG. 5, a disk arthroplasty device 110, similar to that shown in FIGS. 1-4, is shown. The disk arthroplasty device 110 comprises an ellipsoidally-shaped ball 146 and socket 126, oriented so that their greatest lengths are disposed along a first axis transverse to the anterior and posterior ends 158 and 160 respectively and their shortest lengths are disposed along a second axis which is perpendicular to the first axis along surface 156. In one preferred embodiment, the radius of the ellipsoidal ball and socket configurations is 0.322 inches along the first axis and 0.173 inches along the second axis. In another embodiment, the radius of the ball and socket configurations is 0.431 inches along the first axis and 0.256 inches along the second axis. Generally, the greater the ball radii, the greater the resistance to compressive, rotational and axial shear loading.

The center of rotation 165 of the arthroplasty device 110 is located posteriorly, at 65 percent of the length between the anterior end 158 and posterior end 160, to match the normal lumbar spine center of rotation. The present invention further contemplates locating the device 110 center of rotation elsewhere to match centers of rotation in other areas of the spine.

As seen in FIGS. 5 and 7, the first joint surface 136 is sloped away from socket 126 while the second joint surface 156 remains flat, although the present invention contemplates sloping either one or both of joint surfaces 136 and 156. The degree of slope determines the amount of relative rotation between joint surfaces 136 and 156 respectively and the first joint surface 136 is sloped to provide for up to 5 degrees of lateral bending in either direction, up to 5 degrees of extension and up to 15 degrees of flexion. In the preferred embodiment, the first joint surface 136 is sloped to provide 5 degrees of lateral bending in either direction, 5 degrees of extension and 15 degrees of flexion. In this embodiment, ball 146 and socket 126 may be configured to have a predetermined fit to permit axial rotation of up to 5 degrees in either direction as shown at 170 in FIG. 5. Any further rotation is inhibited due to the elongated nature of ball 146 and socket 126.

FIGS. 6 and 7 show the device arthroplasty device 110 of FIG. 5 positioned between a first and second vertebra 12 and 14 respectively. FIG. 6 shows an anterior view of device arthroplasty disk 110 in place of a natural disk and FIG. 7 shows a side view of the same. Both FIGS. 6 and 7 show the device arthroplasty device 110 of FIG. 5 in cross-section.

Figure 8:
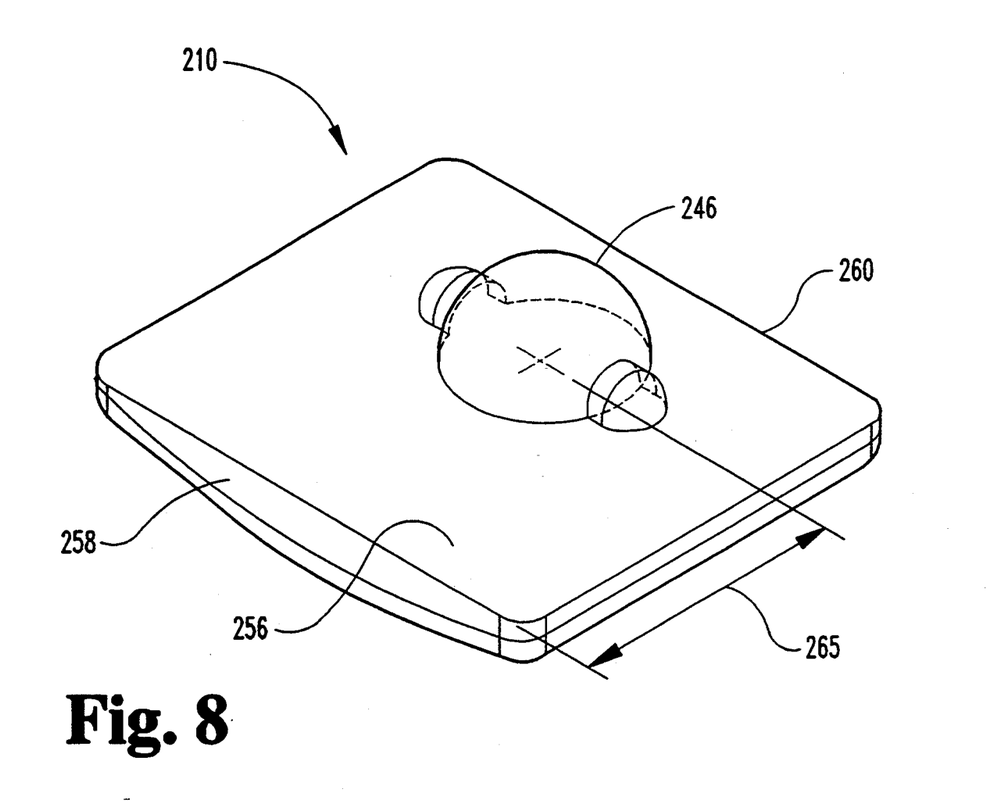
FIG. 8 is a perspective view of the lower member of a disk arthroplasty device in accordance with a further embodiment of the invention.
Figure 9:
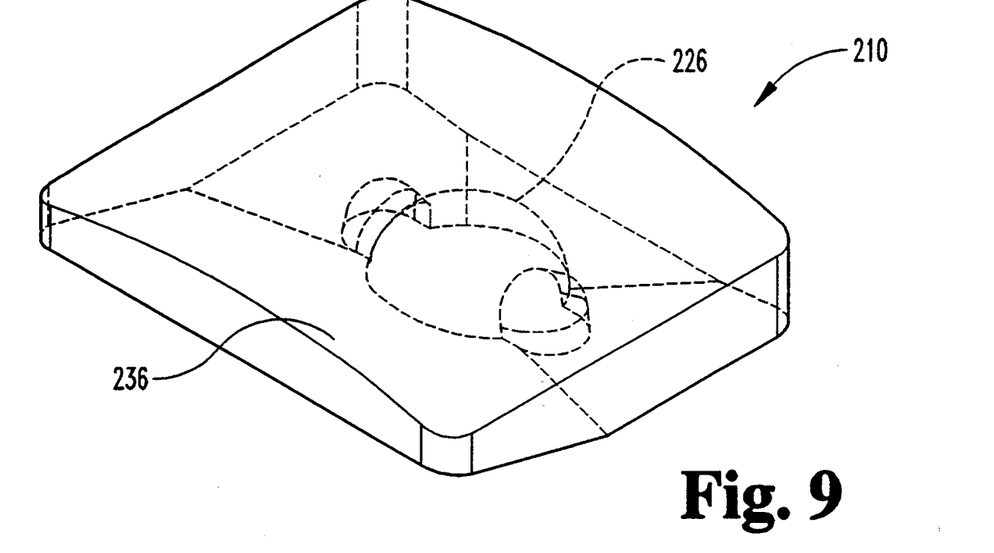
FIG. 9 is a perspective view of the upper member of a disk arthroplasty device with a socket configuration corresponding to the ball configuration of FIG. 8 shown in phantom.

Referring now to FIGS. 8 and 9, another embodiment of the arthroplasty device of the present invention is shown. The device 210 ball 246 of FIG. 8 and socket 226 of FIG. 9 are spherically-shaped with partially cylindrical shapes at the transverse ends.

The center of rotation 265 of the arthroplasty device 210 is located posteriorly, at 65 percent of the length between the anterior end 258 and posterior end 260, to match the normal lumbar spine center of rotation. The present invention further contemplates locating the device 210 center of rotation elsewhere to match centers of rotation in other areas of the spine.

As seen in FIG. 9, the first joint surface 236 is sloped away from socket 226 while the second joint surface 256 remains flat, although the present invention contemplates sloping either one or both of joint surfaces 236 and 256. The degree of slope determines the amount of relative rotation between joint surfaces 236 and 256 respectively and the first joint surface 236 is sloped to provide for up to 5 degrees of lateral bending in either direction, up to 5 degrees of extension and up to 15 degrees of flexion. In the preferred embodiment, the first joint surface 236 is sloped to provide 5 degrees of lateral bending in either direction, 5 degrees of extension and 15 degrees of flexion. In this embodiment, ball 246 and socket 226 may be configured to have a predetermined fit to permit axial rotation of up to 5 degrees in either direction as shown generally at 170 for disk arthroplasty device 110. Any further rotation is inhibited due to the partially cylindrical shapes of ball 246 and socket 226.

Figure 10:
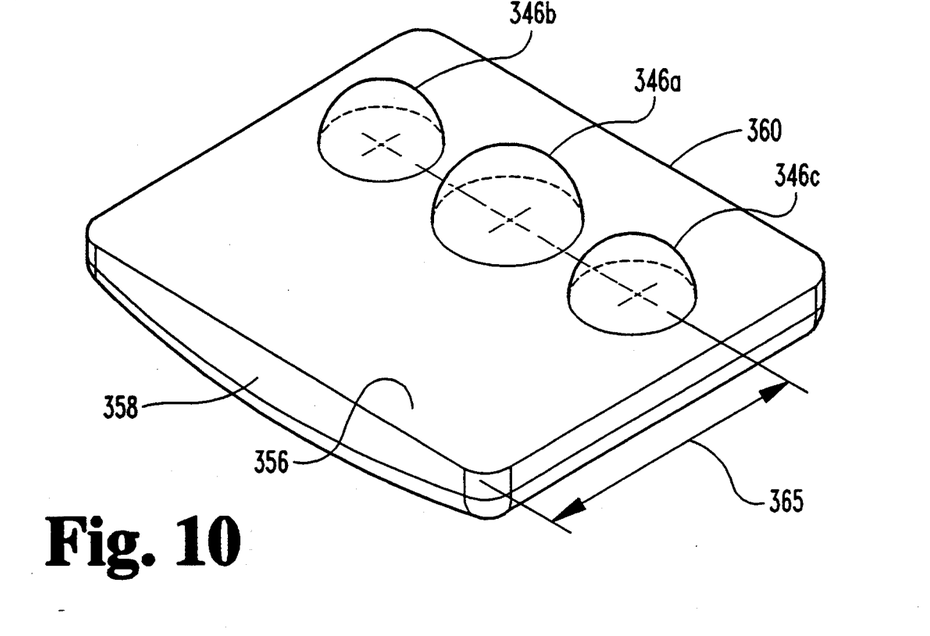
FIG. 10 is a perspective view of the lower member of a disk arthroplasty device in accordance with a further embodiment of the invention with the ball configuration shown in phantom.
Figure 11:
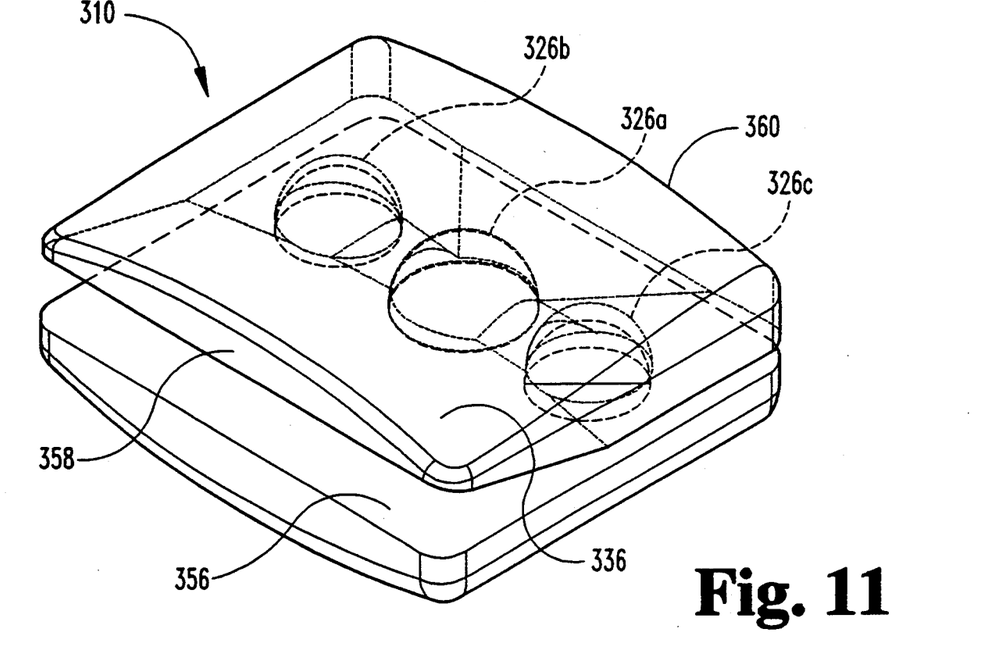
FIG. 11 is a perspective view of a disk arthroplasty device with a socket configuration corresponding to the ball configuration of FIG. 10.

Referring now to FIGS. 10 and 11, another embodiment of arthroplasty device 310 is shown wherein the ball portion 346 of FIG. 10 and corresponding socket portion 326 of FIG. 11 are comprised of three spherical shapes 346(a), 346(b), 346(c), 326(a), 326(b) and 326(c) respectively. Ball 346(a) and socket 326(a) are sized to be larger in radius than the respective (b) and (c) spheres and sockets. In addition, ball and socket portions 346(b), 346(c), 326(b) and 326(c) are sized to have equal radii and be equally spaced in transverse directions from ball and socket portions 346(a) and 326(a) as shown in FIGS. 10 and 11.

The center of rotation 365 of the arthroplasty device 310 is located posteriorly, at 65 percent of the length between the anterior end 358 and posterior end 360, to match the normal lumbar spine center of rotation. The present invention further contemplates locating the device 310 center of rotation elsewhere to match centers of rotation in other areas of the spine.

As seen in FIG. 11, the first joint surface 336 is sloped away from socket 326 while the second joint surface 356 remains flat, although the present invention contemplates sloping either one or both of joint surfaces 336 and 356. The degree of slope determines the amount of relative rotation between joint surfaces 336 and 356 respectively and the first joint surface 336 is sloped to provide for up to 5 degrees of lateral bending in either direction, up to 5 degrees of extension and up to 15 degrees of flexion. In the preferred embodiment, first joint surface 336 is sloped to provide 5 degrees of lateral bending in either direction, 5 degrees of extension and 15 degrees of flexion. In this embodiment, ball portion 346 and socket portion 326 may be configured to have a predetermined fit to permit axial rotation of up to 5 degrees in either direction as shown generally at 170 for disk arthroplasty device 110. Any further rotation is inhibited due to the location of ball 346(b) and corresponding socket 326(b) and ball 346(c) and corresponding socket 326(c).

The design of FIGS. 10 and 11 permit the highest area of contact between ball portion 346 and socket portion 326 while maintaining the required constraint to axial rotation.

Figure 12:
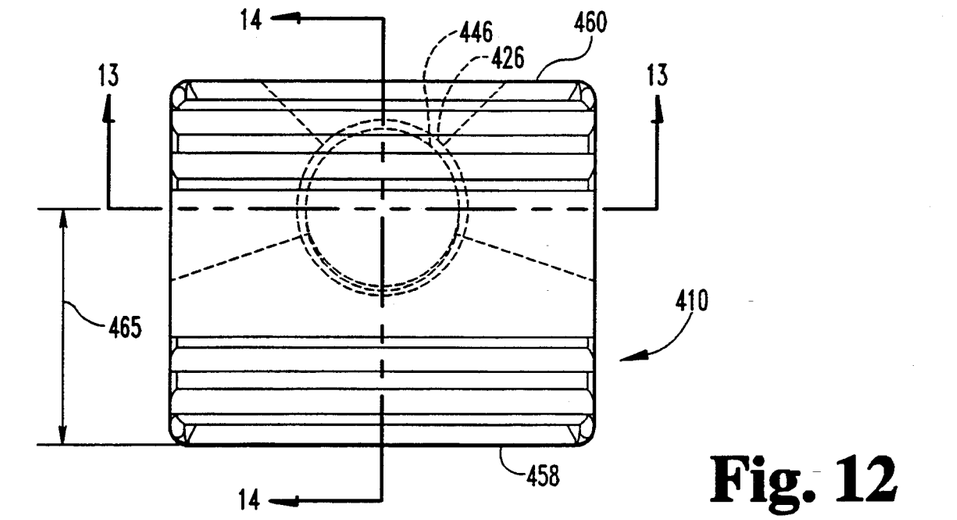
FIG. 12 shows a top elevational view of a disk arthroplasty device with another ball configuration according to the present invention.
Figure 13:
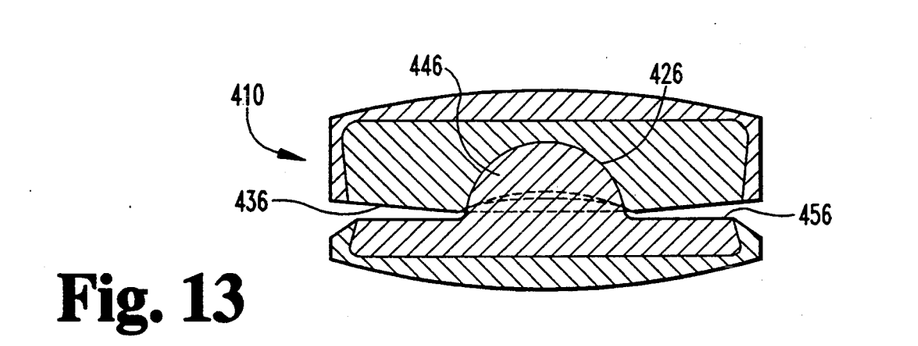
FIG. 13 is a cross-section of the disk arthroplasty device of FIG. 12 along section lines 13—13.
Figure 14:
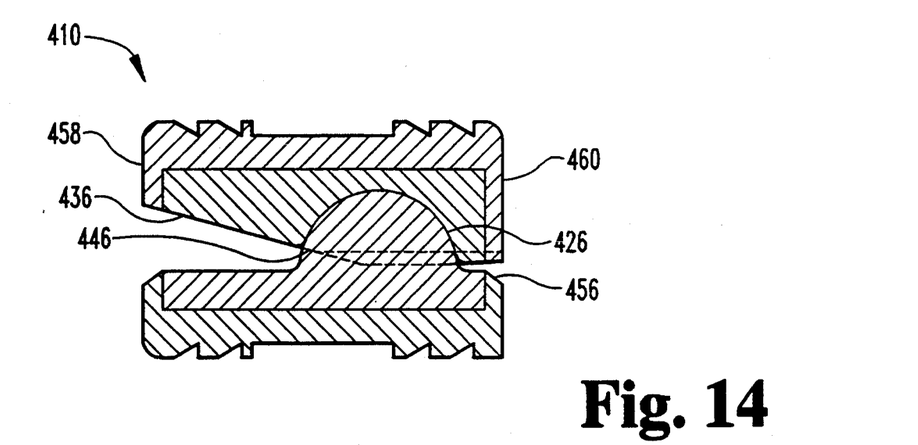
FIG. 14 is a cross-section of the disk arthroplasty device of FIG. 12 along section lines 14—14.

Referring now to FIGS. 12–14, another preferred embodiment of arthroplasty device 410 is shown wherein the ball 446 and socket 426 are spherically shaped. This embodiment permits virtually unrestrained rotation about the long axis of the spine. Under normal circumstances, rotation should be restricted to protect the facets. However, if only a small portion of the annulus is removed to insert disk arthroplasty device 410, the remaining annulus is believed to provide significant resistance to rotation, thereby allowing only normal physiological loading of the facets with this design. Restriction of axial rotation is therefore no longer necessary and the disk arthroplasty device may therefore allow 3 degrees of freedom mimicking the normal intervertebral disk movements of flexion/extension, lateral bending and axial rotation. Anterior/posterior shear, lateral shear and axial compression are restricted with this particular embodiment.

The center of rotation 465 of the arthroplasty device 410 is located posteriorly, at 65 percent of the length between the anterior end 458 and posterior end 460, to match the normal lumbar spine center of rotation. The present invention further contemplates locating the device 410 center of rotation elsewhere to match centers of rotation in other areas of the spine.

As seen in FIGS. 13 and 14, the first joint surface 436 is sloped away from socket 426 while the second joint surface 456 remains flat, although the present invention contemplates sloping either one or both of joint surfaces 436 and 456. The degree of slope determines the amount of relative rotation between joint surfaces 436 and 456 respectively and the first joint surface 436 is sloped to provide for up to 5 degrees of lateral bending in either direction, up to 5 degrees of extension and up to 15 degrees of flexion. In the preferred embodiment, the first joint surface is sloped to provide 5 degrees of lateral bending in either direction, 5 degrees of extension and 15 degrees of flexion.

Figure 15:
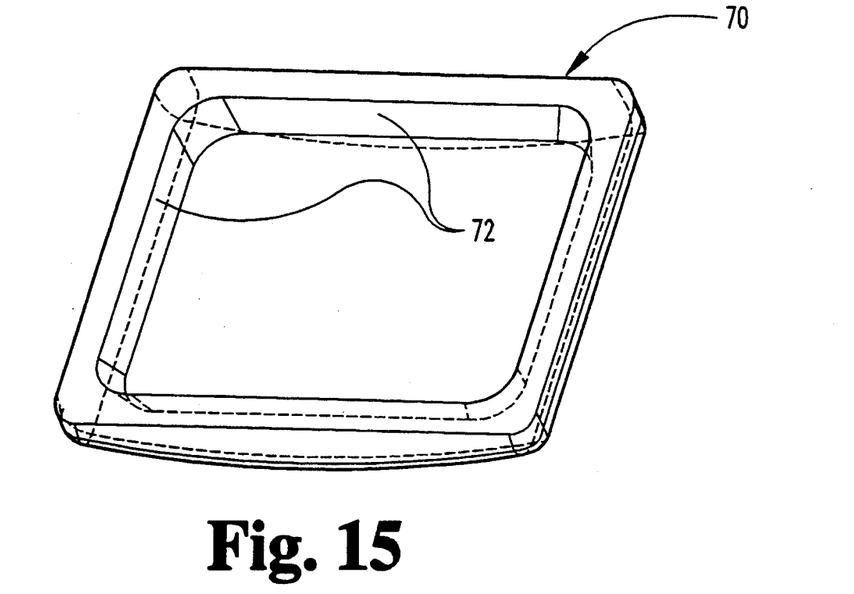
FIG. 15 is a top perspective view of an insert cup according to the present invention.
Figure 16:
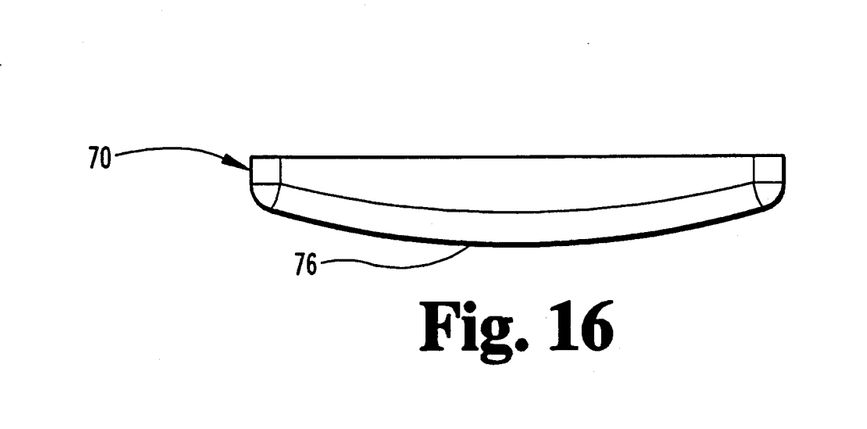
FIG. 16 is a side elevational view of the insert cup of FIG. 15.
Figure 17:
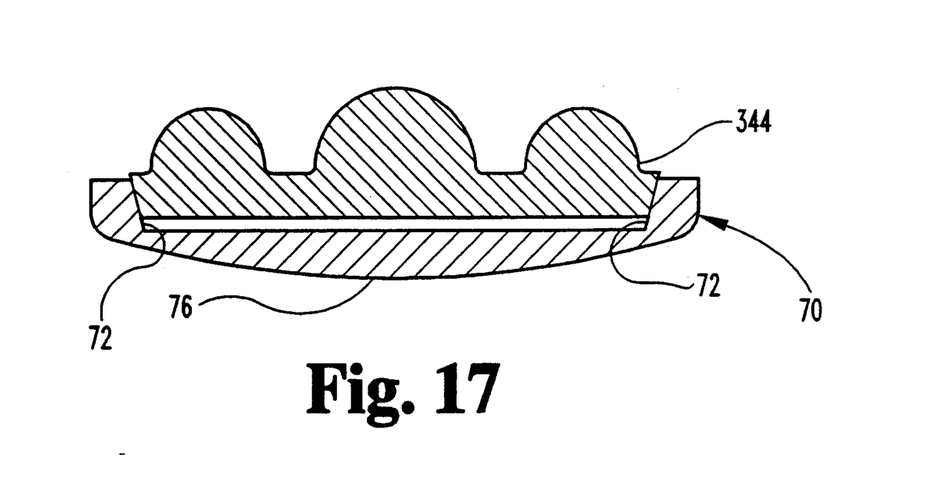
FIG. 17 is a side elevational view of the insert cup of FIG. 15 with the lower member of a disk arthroplasty device mounted therein.
Figure 18:
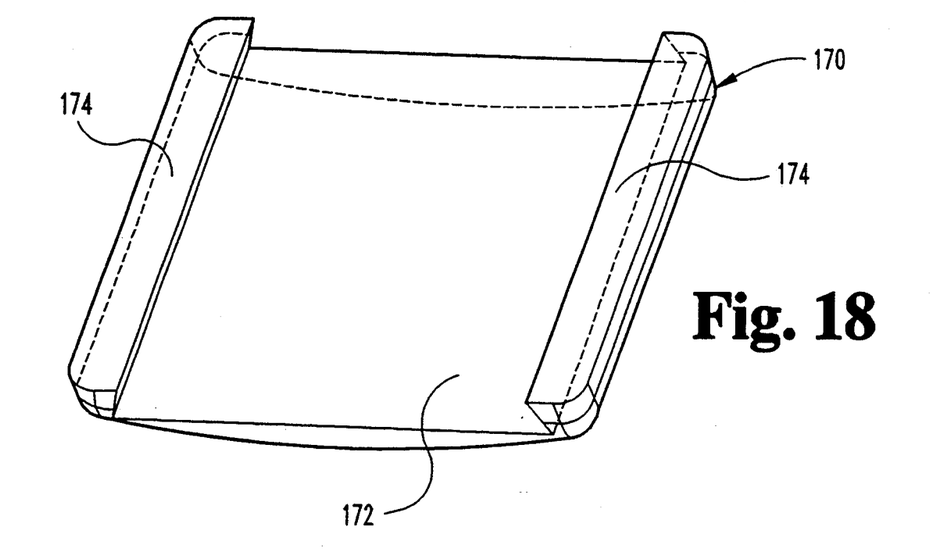
FIG. 18 is a top perspective view of another insert cup according to the present invention.
Figure 19:
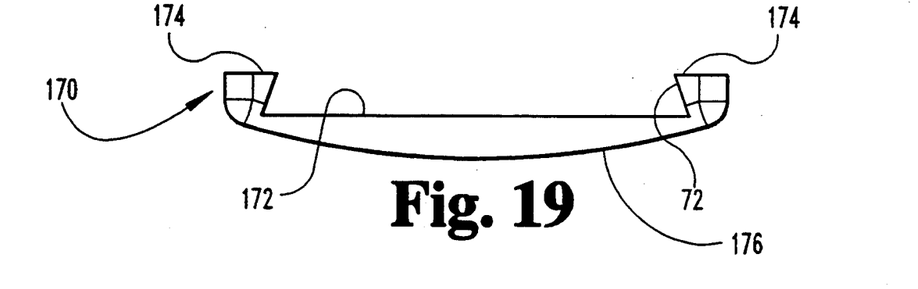
FIG. 19 is a side elevational view of the insert cup of FIG. 18.

Referring now to FIGS. 15–22, each embodiment of the disk arthroplasty device of the present invention may be fastened to insert cups before surgical implantation. FIGS. 15–17 show one embodiment of an insert cup 70. The insert cup 70 is configured ho be fastened to either the upper side of the first member, such as member 324, or the lower side of the second member, such as member 344 as shown in FIG. 17, at its surface 72 by press fitting a disk arthroplasty member within the insert cup. The present invention also contemplates other means for fastening the insert cup 70 to a disk arthroplasty device surface such as with a body-compatible adhesive, tape, solder attachment or clip mechanism. Insert cup 70 is provided with an engaging surface 76 for engaging either vertebral surface as shown in FIGS.

5 and 6. Engaging surface 76 is generally convexly shaped about an axis perpendicular to the spine as shown in FIG. 5. This configuration follows the natural contours of the top and bottom vertebrae surfaces and acts to stabilize the device with respect to axial rotation and anterior/posterior shear.

Figure 20:
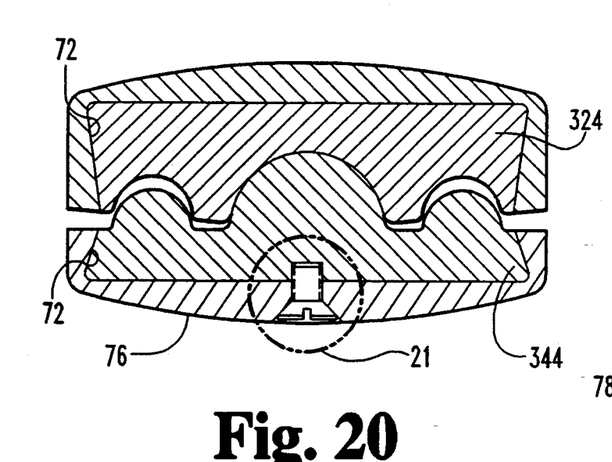
FIG. 20 is a cross sectional view of a disk arthroplasty device mounted within a pair of insert cups of FIG. 18 and showing a screw attachment of the arthroplasty device to one of the insert cups.
Figure 21:
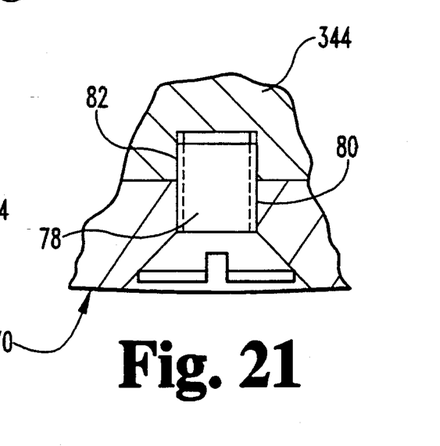
FIG. 21 is an enlarged version of the circled area of FIG. 20 showing a screw attachment of a disk arthroplasty member to the insert cup of FIG. 18.

FIGS. 18–21 show another embodiment of insert cup 170 with a receiving surface 172 and flanges 174 for slidably receiving the outer surface of a first member, such as member 324, or the outer surface of a second member, such as member 344, as shown in FIG. 20. Insert cup 170 is provided with a convex engaging surface 176 for engaging either vertebral surface, identical to the embodiment shown by insert cup 70. A disk arthroplasty device member is attached to insert cup 170 by screwing the cup 170 to a member, such as member 344, as shown in FIG. 20. As shown in detail in FIG. 21, the screw 78 is counter-sunk through opening 80 in insert cup 170 and engages another opening 82 in member 344.

The preferred material for either insert cup 70 or 170 is a metal, such as titanium. The insert cups may be formed by a variety of known processes such as machining or molding and in one embodiment of the present invention, the insert cups are molded. Using titanium insert cups with a disk arthroplasty device of the present invention provides various benefits such as providing tensile support to the structure and maintaining the first and second member material in compression and providing a structure wherein the disk arthroplasty device members can remain a single size while the insert cup sizes may be more easily and cheaply varied by either adding or reducing metal thickness.

Figure 22:
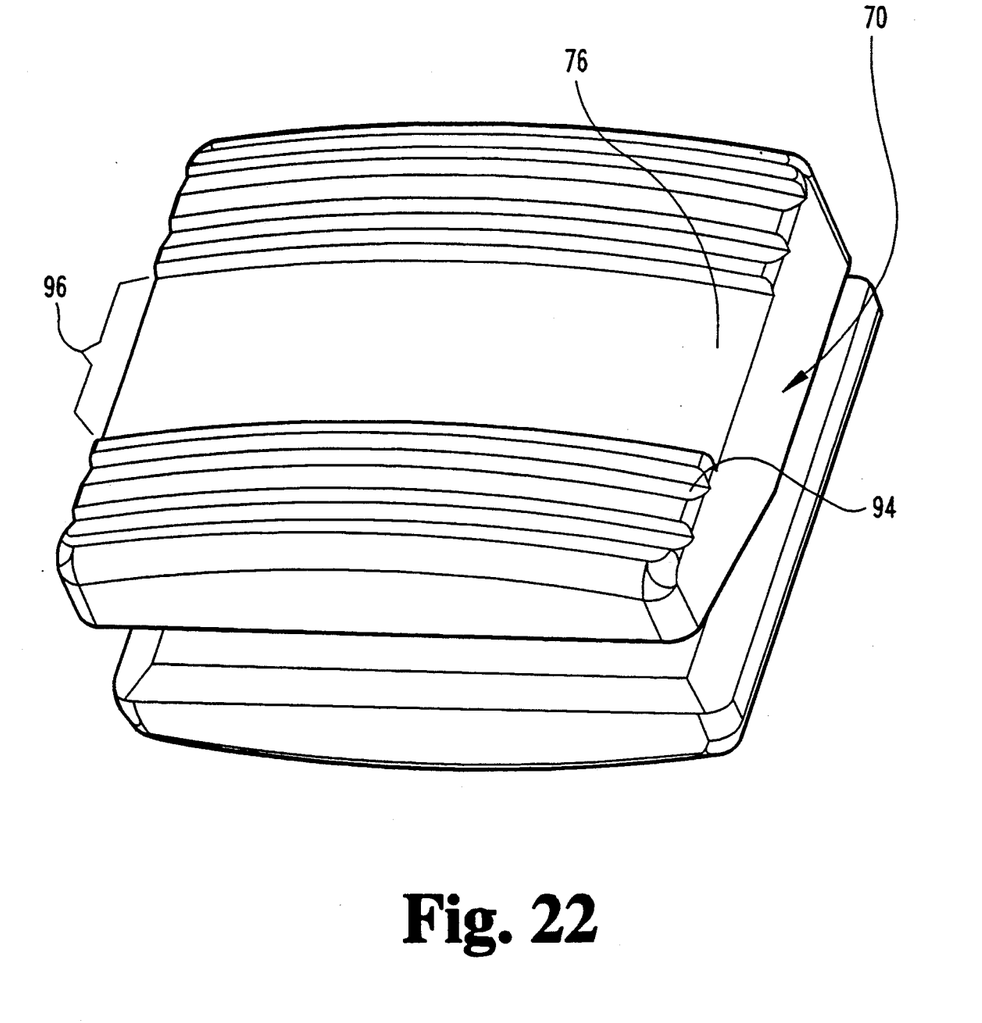
FIG. 22 shows a top perspective view of an insert cup incorporating rows of resisting teeth and a bead pocket.

Another benefit of using titanium insert cups with a disk arthroplasty device is that the insert cups provide a surface to which resisting fins, spikes or teeth can be more easily attached than to ceramic. FIG. 6 shows the attachment of resisting fins 92 to the anterior ends of the outer surface of an insert cup. These fins act to enhance the resistance of an arthroplasty device to axial rotation and may be attached to the insert cups by known processes such as machining, soldering, welding and gluing. In one embodiment, the fins are welded to the insert cups. FIG. 22 shows rows of teeth 94 affixed to the surface of insert cup 70 that allow easy insertion of the arthroplasty device into a disk space, but resist expulsion in the opposite direction. Although any of the aforementioned attachment processes may be used to attach the rows of teeth 94 to the insert cups, in one embodiment these teeth are formed into during the machining process of the insert cups.

Yet another benefit of using titanium insert cups with a disk arthroplasty device is that insert cups provide a surface that coatings may easily adhere to. FIGS. 6 and 7 show the application of a titanium bead coating 90 to the outer surfaces of the insert cups to promote bony ingrowth fixation. A variety of known technologies may be used to apply a coating such as sintering or spraying and in one embodiment, the titanium bead coating 90 is sprayed onto the outer surface of the insert cups. FIG. 22 shows a bead pocket 96 that is provided between the sets of teeth rows 94, for receiving a coating of titanium beads. In the embodiment of FIG. 22, the rows of teeth resist expulsion of the disk arthroplasty device opposite to the direction of device insertion. The titanium bead coating disposed within bead pocket 96 then promotes bony ingrowth fixation which acts to hold the outer surface of the insert cups in place and to enhance resistance to movement of the insert cups in any direction.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An intervertebral disk arthroplasty device adapted to replace a disk between a first vertebra and a second vertebra in a spine, said arthroplasty device comprising:
    a first member for engaging the first vertebra having a first joint surface, a first posterior end and a first anterior end, said ends defining a transverse midline therebetween, said midline being equidistant from said first posterior end and said first anterior end;
    a second member for engaging the second vertebra having a second joint surface facing said first joint surface, and second posterior and anterior ends juxtaposed with corresponding ones of said first posterior and anterior ends; and
    a ball and socket joint between said first and second members defined in said first and second joint surfaces and disposed between said midline and said first posterior end, said ball and socket joint configured to permit relative rotation between said first member and said second member about a first axis parallel to said transverse midline and a second axis perpendicular to said first axis and lying in a sagittal plane of the spine, wherein one of said first and second joint surfaces is inclined away from said ball and socket joint toward its respective first or second joint member, entirely around said joint, and the other of said first and second joint surfaces is substantially parallel to a plane defined by said first and second axes around said joint.

2. The intervertebral disk arthroplasty device of claim 1, wherein said inclined surface includes a first inclined face extending from said first axis to said anterior end at a first angle, a second inclined face extending from said first axis to said posterior end at a second angle, third and fourth inclined faces extending from said second axis in opposite directions away from said second axis and parallel to said first axis at third and fourth angles respectively, said first, second, third and fourth angles being measured relative to the other of said first and second joint surfaces.

3. The intervertebral disk arthroplasty device of claim 2, wherein said third and fourth angles are sized to permit relative rotation up to a first predetermined angle between said first and second members about said second axis before said first joint surface contacts said second joint surface.

4. The intervertebral disk arthroplasty device of claim 3, wherein said second angle is sized to permit relative rotation between said first and second members, up to a second predetermined angle in a direction toward said posterior ends, about said first axis before said first joint surface contacts said second joint surface.

5. The intervertebral disk arthroplasty device of claim 4, wherein said first angle is sized to permit relative rotation between said first and second members, up to a third predetermined angle in a direction toward said anterior ends, about said first axis before said first joint surface contacts said second joint surface.

6. The intervertebral disk arthroplasty device of claim 5, wherein said ball and socket joint includes a ball portion defined on said first joint surface of said first member along said first axis and a socket portion correspondingly defined in said second joint surface of said second member to receive said ball portion therein.

7. The intervertebral disk arthroplasty device of claim 6, wherein said ball portion is circular in cross section along said first joint surface.

8. The intervertebral disk arthroplasty device of claim 1, wherein said first and second members are made of zirconia.

9. The intervertebral disk arthroplasty device of claim 1, wherein said first and second members are made of alumina.

10. An intervertebral disk arthroplasty device adapted to replace a disk between a first vertebra and a second vertebra in a spine, said arthroplasty device comprising:
- a first member for engaging the first vertebra having a first joint surface, a first posterior end and a first anterior end, said ends defining a transverse midline therebetween;
- a second member for engaging the second vertebra having a second joint surface facing said first joint surface, and second posterior and anterior ends juxtaposed with corresponding ones of said first posterior and anterior ends;
- an elongated ball and socket joint between said first and second members defined in said first and second joint surfaces, said elongated ball and socket joint including;
    - a ball portion defined on said first joint surface of said first member and elongated along a first axis parallel to said midline, and
    - a socket portion correspondingly defined in said second joint surface of said second member for receiving said elongated ball portion therein with a predetermined fit to permit a predetermined relative rotation between said first and second members about a second axis perpendicular to said first and second joint surfaces before said elongated ball portion contacts said corresponding socket portion, wherein one of said first and second joint surfaces is inclined away from said ball and socket joint toward its respective first or second joint member, entirely around said joint, and the other of said first and second joint surfaces is substantially parallel to a plane defined by said first and second axes around said joint.

11. The intervertebral disk arthroplasty device of claim 10, wherein said elongated ball and socket portions are ellipsoidal in cross section in a plane parallel to said first joint surface.

12. The intervertebral disk arthroplasty of claim 10, wherein said elongated ball and socket portions are partially circular in cross section in a plane parallel to said first joint surface and include opposite ends formed in a partially cylindrical shape.

13. The intervertebral disk arthroplasty device of claim 10, wherein said elongated ball and socket joint includes a plurality of separate ball portions and corresponding socket portions.

14. The intervertebral disk arthroplasty device of claim 13, wherein said plurality of ball and socket portions include:
- a first ball and socket portion; and
- second and third ball and socket portions spaced on opposite sides of said first ball portion and equidistant from said first ball portion.

15. The intervertebral disk arthroplasty device of claim 14, wherein said first, second and third ball portions are circular in cross section in a plane parallel to said first joint surface, said first ball portion having a radius greater than the radii of said second and third ball portions.

16. The intervertebral disk arthroplasty device of claim 15, wherein said second and third ball portions have equal radii.

* * * * *

UNITED STATES PATENT AND TRADEMARK OFFICE
CERTIFICATE OF CORRECTION

PATENT NO. : 5,425,773
DATED      : June 20, 1995
INVENTOR(S) : Lawrence M. Boyd et al.

It is certified that error appears in the above-identified patent and that said Letters Patent is hereby corrected as shown below:

Column 2, line 56, please change "Dead" to "bead".

Column 8, line 58, please change "ho" to "to".

Signed and Sealed this

Twenty-eighth Day of November 1995

Attest:

BRUCE LEHMAN

Attesting Officer

Commissioner of Patents and Trademarks